United States Patent [19]

Takahashi et al.

[11] Patent Number: 5,710,346
[45] Date of Patent: Jan. 20, 1998

[54] 2,2-BIS(3,5-DISUBSTITUTED-4-HYDROXYPHENYL) PROPANE DERIVATIVE, PROCESS FOR PRODUCTION THEREOF, AND PROCESS FOR PRODUCING PYROGALLOL USING SAID DERIVATIVE

[75] Inventors: Masakazu Takahashi, Tokyo; Tomonori Miyazaki, Shizuoka-ken; Chika Maejima, Shizuoka-ken; Yoshikazu Kimura, Shizuoka-ken, all of Japan

[73] Assignee: Ihara Chemical Industry Co., Ltd., Tokyo, Japan

[21] Appl. No.: 454,157

[22] PCT Filed: Oct. 21, 1994

[86] PCT No.: PCT/JP94/01775

§ 371 Date: Jun. 15, 1995

§ 102(e) Date: Jun. 15, 1995

[87] PCT Pub. No.: WO95/11211

PCT Pub. Date: Apr. 27, 1995

[30] Foreign Application Priority Data

Oct. 22, 1993 [JP] Japan .................. 5-287472

[51] Int. Cl.$^6$ ........................... C07C 39/16
[52] U.S. Cl. ........................... 568/723; 568/722
[58] Field of Search ........................... 568/722, 723

[56] References Cited

U.S. PATENT DOCUMENTS

| | | | |
|---|---|---|---|
| 4,716,252 | 12/1987 | Wagner et al. | 568/729 |
| 4,814,520 | 3/1989 | Nakagawa | 568/723 |

FOREIGN PATENT DOCUMENTS

| | | |
|---|---|---|
| 41-16165 B1 | 9/1966 | Japan . |
| 51-105020 A | 9/1976 | Japan . |
| 53-130642 A | 11/1978 | Japan . |
| 58-14410 B2 | 3/1983 | Japan . |
| 60-34529 B2 | 8/1985 | Japan . |
| 60-39057 B2 | 9/1985 | Japan . |
| 62-33130 A | 2/1987 | Japan . |
| 1-15489 B2 | 3/1989 | Japan . |
| 3-7240 A | 1/1991 | Japan . |
| 5-170687 A | 7/1993 | Japan . |

OTHER PUBLICATIONS

Abstract to Hosaka et al., EP 211667 A2, Feb. 25, 1987.

Primary Examiner—Marianne M. Cintins
Assistant Examiner—Dwayne C. Jones
Attorney, Agent, or Firm—Oblon, Spivak, McClelland, Maier & Neustadt, P.C.

[57] ABSTRACT

The present invention provides a 2,2-bis(3,5-disubstituted-4-hydroxyphenyl) propane derivative represented by general formula (1)

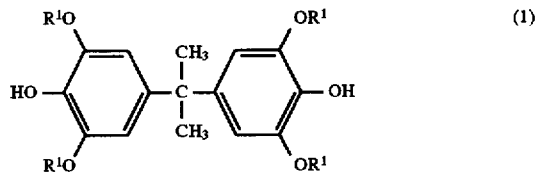

wherein each $R^1$ represents a hydrogen atom or a lower alkyl group; a process for producing such propane derivative; and a process for producing pyrogallol using such propane derivative. The compound of the present invention has by itself a periphyton-controlling activity required for the active ingredient used in a periphyton-controlling agent such as antifouling paint for ship's bottom, antifouling agent for fishing net, or the like. Further, by decomposing the above compound with an alkali or an acid, pyrogallol can be produced industrially without using any natural material.

4 Claims, No Drawings

2,2-BIS(3,5-DISUBSTITUTED-4-HYDROXYPHENYL) PROPANE DERIVATIVE, PROCESS FOR PRODUCTION THEREOF, AND PROCESS FOR PRODUCING PYROGALLOL USING SAID DERIVATIVE

This application is a 371 of PCT/JP94/01775 which was filed on Oct. 21, 1994.

TECHNICAL FIELD

The present invention relates to a novel 2,2-bis(3,5-disubstituted-4-hydroxyphenyl)propane derivative, a process for production thereof, and a process for producing pyrogallol using the propane derivative.

More particularly, the present invention relates to a 2,2-bis(3,5-disubstituted-4-hydroxyphenyl)propane derivative which has by itself a periphyton (e.g., marine fouling organism)-controlling activity required for the active ingredient used in an antifouling paint for ship's bottom, an antifouling agent for fishing net, or the like and which also is useful as a material for pyrogallol production; a process for producing the propane derivative industrially; and a process for producing pyrogallol industrially by using the propane derivative.

BACKGROUND ART

The 2,2-bis(3,5-disubstituted-4-hydroxyphenyl)propane derivative provided by the present invention is a novel compound which is not described in any literature, and it has been unknown that the compound has by itself a periphyton-controlling activity and also can be used as a suitable material for industrial production of pyrogallol.

Up to this time, pyrogallol has been produced by heating gallic acid in an autoclave at 200°–210° C. for 30 minutes and subjecting the resulting product to decoloring, filtration and vaporization. This process has not been satisfactory as an industrial process, for example, because the raw material is a natural product, is difficult to procure stably, and is expensive.

The objects of the present invention are to provide a novel 2,2-bis(3,5-disubstituted-4-hydroxyphenyl)propane derivative, a process for production thereof, and a process for producing pyrogallol using the propane derivative.

The present inventors made an extensive study in order to provide a useful and novel 2,2-bis(3,5-disubstituted-4-hydroxyphenyl)propane derivative and a process for production thereof. As a result, the present inventors found out that the 2,2-bis(3,5-disubstituted-4-hydroxyphenyl)propane derivative can easily be obtained by reacting a 2,2-bis(3,5-dihalogeno-4-hydroxyphenyl)propane (this is easily available) with a metal alkoxide.

The present inventors further found out that the above propane derivative has by itself a periphyton-controlling activity required for the active ingredient used in an antifouling paint for ship's bottom, an antifouling agent for fishing net, or the like and also that by decomposing the propane derivative with an alkali or an acid, pyrogallol can be obtained easily. The present invention has been completed based on the above finding.

DISCLOSURE OF THE INVENTION

The present invention provides:

[1] a 2,2-bis(3,5-disubstituted-4-hydroxyphenyl)propane derivative represented by general formula (1)

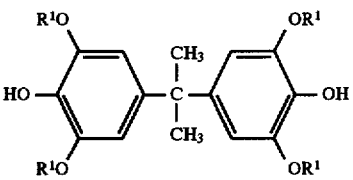

wherein each $R^1$ represents a hydrogen atom or a lower alkyl group,

[2] a process for producing a 2,2-bis[3,5-di(lower alkoxy)-4-hydroxyphenyl]propane derivative, which is characterized by reacting a 2,2-bis(3,5-dihalogeno-4-hydroxyphenyl) propane derivative represented by general formula (2)

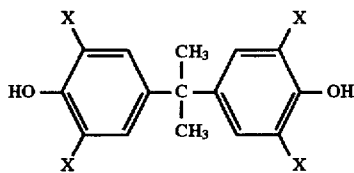

wherein each X represents a halogen atom, with a metal alkoxide represented by general formula (3)

wherein each $R^2$ represents a lower alkyl group, M represents an alkali metal or an alkaline earth metal, and n represents an integer of 1 or 2,

[3] a process for producing 2,2-bis(3,4,5-trihydroxyphenyl)propane, which is characterized by dealkylating the above 2,2-bis[3,5-di(lower alkoxy)-4-hydroxyphenyl]propane, and

[4] a process for producing pyrogallol, which is characterized by decomposing, with an alkali or an acid, a 2,2-bis(3,5-disubstituted-4-hydroxyphenyl)propane derivative represented by general formula (1)

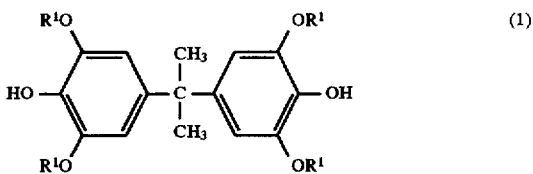

wherein each $R^1$ has the same definition as given above.

The term "lower" used in the present specification refers to that the compound or substituent appearing after the term has 1–4 carbon number.

The present invention is described in detail below

Specific examples of the 2,2-bis(3,5-disubstituted-4-hydroxyphenyl)propane derivative, which is the present compound represented by general formula (1), include compounds of general formula (1) wherein each substituent $R^1$ is a lower alkyl group, i.e. 2,2-bis([3,5-di(lower alkoxy)-4-hydroxyphenyl]propanes. They are more specifically compounds of general formula (1) wherein each of the 3-and 5-positions of the phenyl rings is substituted with an alkoxy group of 1–4 carbon number, i.e. 2,2-bis([3,5-di(lower alkoxy)-4-hydroxyphenyl]propanes such as 2,2-bis(3,5-dimethoxy-4-hydroxyphenyl)propane, 2,2-bis(3,5-diethoxy-4-hydroxyphenyl)propane, 2,2-bis(3,5-dipropoxy-4-hydroxyphenyl)propane, 2,2-bis(3,5-diisopropoxy-4-hydroxyphenyl)propane, 2,2-bis(3,5-dibutoxy-4-hydroxyphenyl)propane, 2,2-bis(3,5-diisobutoxy-4- hydroxyphenyl)propane, 2,2-bis(3,5-di-sec-butoxy-4-hydroxyphenyl)propane, 2,2-bis(3,5-di-tert-butoxy-4-hydroxyphenyl)propane and the like. Specific examples of the compound of general formula (1) include also a compound of general formula (1) wherein each substituent $R^1$ is a hydrogen atom, i.e. 2,2-bis(3,4,5-trihydroxyphenyl) propane.

Then, description is made on the production of the present compound.

The present compound, i.e. the 2,2-bis(3,5-disubstituted-4-hydroxyphenyl)propane derivative (1) can be produced by reacting a 2,2-bis(3,5-dihalogeno-4-hydroxyphenyl)propane (2) with a metal alkoxide (3) in the presence or absence of a catalyst in an appropriate solvent (when each substituent $R^1$ is a lower alkyl group) and further dealkylating the resulting product, i.e. a 2,2-bis([3,5-di(lower alkoxy)-4-hydroxyphenyl]propane (when each substituent $R^1$ is a hydrogen atom).

In the 2,2-bis(3,5-dihalogeno-4-hydroxyphenyl)propane (2) which is a material, the substituent X is a halogen atom. Therefore, the compound (2) can be exemplified by 2,2-bis (3,5-dibromo-4-hydroxyphenyl)propane and 2,2-bis(3,5-dichloro-4-hydroxyphenyl)propane. Of these, particularly preferable is 2,2-bis(3,5-dibromo-4-hydroxyphenyl)propane which is commercially available as Tetrabromobisphenol A (trade name), for its easy industrial availability.

In the general formula (3) for metal alkoxide, the lower alkyl group represented by $R^2$ includes alkyl groups of 1-4 carbon number such as methyl group, ethyl group, propyl group, isopropyl group, n-butyl group, isobutyl group, sec-butyl group, tert-butyl group and the like. A methyl group or an ethyl group is used preferably. In the same formula, the alkali metal or alkaline earth metal represented by M includes alkali metals such as lithium, sodium, potassium and the like, and alkaline earth metals such as calcium, magnesium, barium and the like. The metal alkoxide (3) having such an $R^2$ and such an M can specifically be exemplified by sodium methoxide, potassium methoxide, sodium ethoxide, potassium ethoxide, sodium propoxide, potassium propoxide, sodium isopropoxide, potassium isopropoxide, sodium n-butoxide, potassium n-butoxide and potassium tert-butoxide. The amount of the metal alkoxide (3) used is 4-20 moles, preferably 4-8 moles per mole of the 2,2-bis(3,5-dihalogeno-4-hydroxyphenyl)propane.

The solvent can be exemplified by aprotic polar solvents such as dimethylformamide, dimethyl sulfoxide and the like; ethers such as diethyl ether, tetrahydrofuran and the like; ketones such as acetone, methyl ethyl ketone, methyl isobutyl ketone and the like; and alcohols such as methanol, ethanol and the like. Preferable are aprotic polar solvents such as dimethylformamide, dimethyl sulfoxide and the like. The amount of the solvent used is 0.01–10 liters, preferably 0.1–5 liters per mole of the material, i.e. the 2,2-bis(3,5-dihalogeno-4-hydroxyphenyl)propane.

As necessary, there can be used, as a catalyst, a copper salt such as copper (I) chloride, copper (I) iodide or the like. Its amount used is 0.01–50 mole %, preferably 0.05–5 mole % based on the material, i.e. the 2,2-bis(3,5-dihalogeno-4-hydroxyphenyl)propane.

The reaction temperature is generally 0°–200° C., preferably 20°–130° C. The reaction pressure is not particularly restricted but is generally atmospheric pressure.

By the above reaction is obtained a compound of general formula (1) wherein $R^1$ is a lower alkyl group, i.e. a 2,2-bis[3,5-di(lower alkoxy)-4-hydroxyphenyl]propane. By dealkylating the compound, there can be obtained a compound of general formula (1) wherein $R^1$ is a hydrogen atom, i.e. 2,2-bis(3,4,5-trihydroxyphenyl)propane.

The dealkylation is conducted generally by using an acid. The acid usable can be exemplified by hydrogen halides such as hydrobromic acid, hydroiodic acid and the like; Lewis acids such as boron tribromide, boron trichloride, phosphorus tribromide and the like; sulfuric acid and p-toluenesulfonic acid. The amount of the acid used is 4–20 moles, preferably 6–10 moles per mole of the material, i.e. 2,2-bis[3,5-di(lower alkoxy)-4-hydroxyphenyl]propane. In view of the property of the acid used, there may be used, as necessary, an appropriate solvent such as water, halogenated hydrocarbon (typically dichloromethane), aromatic hydrocarbon (typically benzene) or the like.

The temperature of the above reaction is −80° to 200° C., preferably −5° to 100° C., and the pressure is generally atmospheric pressure.

The thus obtained compound represented by general formula (1) according to the present invention has a periphyton-controlling activity required for the active ingredient used in an antifouling paint for ship's bottom, an antifouling agent for fishing net, or the like.

The present invention further provides a novel process for producing pyrogallol, which comprises decomposing 2,2-bis(trihydroxyphenyl)propane (4) with an alkali or an acid. In this process, produced pyrogallol can be isolated by reaction-distillation.

Process By Alakali Decomposition

The alkali used for decomposition can be exemplified by hydroxides of alkali metals or alkaline earth metals, such as sodium hydroxide, potassium hydroxide, barium hydroxide, calcium hydroxide and the like. These alkalis may be used in admixture as necessary, but generally sodium hydroxide or potassium hydroxide is used singly. The amount of the alkali used is 0.01–2.0 moles, preferably 0.05–1.0 mole per mole of 2,2-bis(3,4,5-trihydroxyphenyl)propane. The alkali is made into an aqueous solution and is added to a solution of 2,2-bis(3,4,5-trihydroxyphenyl)propane in an appropriate organic solvent (e.g. methanol); the mixture is subjected to distillation to remove the water and the organic solvent; thereby, the alkali can uniformly be mixed with the material.

The above reaction can be conducted generally at 150°–300° C., preferably at 200°–250° C., at atmospheric pressure. It is possible to conduct reaction-distillation at a reduced pressure of 1–300 mmHg, preferably 3–200 mmHg to isolate a product. 15 minutes to 2 hours suffices for the reaction time although it varies depending upon the reaction conditions employed.

Process By Acid Decomposition

The acid usable for decomposition can be exemplified by mineral acids such as sulfuric acid, hydrochloric acid, hydrobromic acid and the like, and organic acids such as p-toluenesulfonic acid, benzenesulfonic acid and the like. The amount of the acid used is 4–20 equivalents, preferably 6–10 equivalents per mole of 2,2-bis(3,4,5-trihydroxyphenyl)propane. The reaction can be conducted generally at 150°–300° C., preferably at 150°–250° C., at atmospheric pressure. It is possible to conduct reaction-distillation at a reduced pressure of 1–200 mmHg, preferably 10–100 mmHg to isolate produced pyrogallol.

In the present process for producing pyrogallol, it is possible to treat a present compound of general formula (1) wherein $R^1$ is a lower alkyl group, i.e. a 2,2-bis[3,5-di(lower alkoxy)-4-hydroxyphenyl)propane derivative under the conditions employed for the acid decomposition of 2,2-bis(3,4,5-trihydroxyphenyl]propane, to convert into an intended product, i.e. pyrogallol in a single-step reaction and then isolate it.

Then, the present invention is described in further detail by way of Examples.

EXAMPLE 1

Production of 2,2-bis(3,5-dimethoxy-4-hydroxyphenyl)propane

Into a 500-ml four-necked flask equipped with a stirrer, a Liebig condenser and a thermometer were fed 60.0 g of 2,2-bis(3,5-dibromo-4-hydroxyphenyl)propane, 85.2 g of 28% sodium methoxide, 87.6 g of 90% sodium methoxide, 300 ml of dimethylformamide and 6 g of copper (I) iodide. The mixture was refluxed with heating, for 4 hours to give rise to a reaction. After the completion of the reaction, the reaction mixture was cooled. Thereto was added 330 ml of water, followed by neutralization with 160.8 g of 35% hydrochloric acid. The neutralized solution was extracted with dichloromethane. The extract was concentrated to vaporize the solvent. To the concentrate was added water, whereby a solid material was obtained. The solid material was dissolved in 120 ml of ethanol. The resulting insolubles were removed by filtration. To the filtrate (the ethanol layer) was added water to separate out crystals. The crystals were collected by filtration and dried to obtain 29 g of 2,2-bis(3,5-dimethoxy-4-hydroxyphenyl)propane as light red crystals.

Data for Confirmation

IR (KBr, $cm^{-1}$): 3530, 3420, 2980, 1615, 1525, 1460, 1420, 1380, 1330, 1230, 1110 NMR ($d_6$–DMSO):δ=8.08 (s, 2H), 6.46 (s, 4H), 3.74 (s, 12H), 1.59 (s, 6H) GC–MS (m/z): 348 ($M^+$), 333, 303, 179

Production of 2,2-bis(3,4,5-trihydroxyphenyl)propane

Into a 200-ml four-necked flask were fed 50 ml of dichloromethane and 7.52 g of boron tribromide. The mixture was stirred by the use of a stirrer piece. The flask was cooled to about 5° C. with ice water. Thereto was dropwise added, in 1 hour, a solution of 1.74 g of the above-obtained 2-(3,5-dimethoxy-4-hydroxyphenyl)propane dissolved in 50 ml of dichloromethane. The mixture was aged for 16 hours with the flask being immersed in ice water, until the flask returned to room temperature, whereby a reaction was allowed to take place. After the completion of the reaction, the reaction mixture was poured into 80 ml of ice water and white insolubles appeared. By continuing stirring for a while, the insolubles were dissolved and the reaction mixture separated into two layers. The aqueous layer was extracted twice with 30 ml of ether. The ether layer obtained was concentrated to obtain 0.59 g of 2,2-bis(3,4,5-trihydroxyphenyl)propane as light red crystals.

Data for Confirmation

IR (KBr, $cm^{-1}$); 3400–3200, 2980, 1715, 1690, 1620, 1540, 1440, 1330, 1190, 1020 NMR ($d_6$–DMSO): δ=7.26 (s, 6H), 6.13 (s, 4H), 1.42 (s, 6H) MS (SIMS) (m/z): 293 ($M^+$+1)

Production of Pyrogallol

Into a 200-ml four-necked flask equipped with a stirrer, a Dimroth condenser and a thermometer were fed 10.0 g of 2,2-bis(3,4,5-trihydroxyphenyl)propane and 44.5 g of a 47% aqueous hydrogen bromide solution. The mixture was reacted for 4 hours under reflux. The reaction mixture was cooled to separate out crystals. Filtration was conducted. The filtrate was neutralized with sodium carbonate and extracted with ethyl acetate. The extract was concentrated to obtain 2.3 g of pyrogallol as a light pink powder. The powder was analyzed by GLC. As a result, the powder had a purity of 95%.

EXAMPLE 2

Production of Pyrogallol

Into a 200-ml four-necked flask equipped with a stirrer, a Dimroth condenser and a thermometer were fed 10.0 g of 2,2-bis(3,5-dimethoxy-4-hydroxyphenyl)propane and 44.5 g of a 47% aqueous hydrogen bromide solution. The mixture was reacted for 4 hours under reflux. The reaction mixture was cooled to separate out crystals. Filtration was conducted. The filtrate was neutralized with sodium carbonate and extracted with ethyl acetate. The extract was concentrated to obtain 1.1 g of pyrogallol as a light pink powder. The powder was analyzed by GLC. As a result, the powder had a purity of 97%.

TEST 1

Test for Control of Periphyton

The nauplii of *Balanus amphitrite*, hatched in an artificial sea water were tamed with a diatom feed to convert them into cypris larvae (settling-stage larvae). 19 ml of an artificial sea water containing 10 of these cypris larvae was placed in a petri dish having a diameter of 5 cm. Thereto was added 1 ml of a test solution prepared by converting 50 mg of the 2-(3,5-dimethoxy-4-hydroxyphenyl)propane (compound 1) produced in Example 1, to an emulsion by the use of an emulsifier of cyclohexanone/Tween 80 (trade name, a product of Atlas Powder Co.)=10/1 and then diluting the emulsion to a desired concentration with an artificial sea water. Then, the petri dish was allowed to stand in a thermostat of 20° C., and the percentage of settlement to dish after 24 hours was measured. The results are shown in Table 1.

TEST 2

A test was conducted in the same manner as in Test 1 except that the test compound was converted from 2,2-bis (3,5-dimethoxy-4-hydroxyphenyl)propane to 2,2-bis(3,4,5-trihydroxyphenyl)propane (compound 2). The results are shown in Table 1.

TABLE 1

| Compound name | Concentration of test solution | Percentage of settlement |
| --- | --- | --- |
| Compound 1 | 10 ppm | 57% |
|  | 100 ppm | 0% |
| Compound 2 | 10 ppm | 67% |
|  | 100 ppm | 10% |

Industrial Applicability

The present invention provides a novel 2,2-bis(3,5-disubstituted-4-hydroxyphenyl)propane derivative which is not described in any literature, a process for production thereof, and a process for producing pyrogallol industrially using the above propane derivative.

The present compound, i.e. the 2,2-bis(3,5-disubstituted-4-hydroxyphenyl)propane derivative has by itself a periphyton-controlling activity required for the active ingredient used in a periphyton-controlling agent such as antifouling paint for ship's bottom, antifouling agent for fishing net, or the like.

The present compound and the present process have made it possible to industrially produce pyrogallol (which is useful as a material for agricultural chemicals and drugs) easily without using any natural material.

What is claimed is:

1. A 2,2-bis (3,5-disubstituted-4-hydroxyphenyl)propane derivative represented by formula (1)

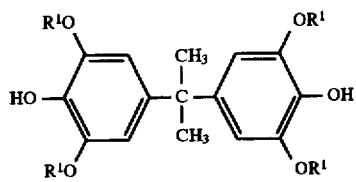 (1)

wherein each $R^1$ represents a hydrogen atom.

2. A process for producing a 2,2-bis[3,5-di(lower alkoxy)-4-hydroxyphenyl]propane derivative, which is characterized by reacting a 2,2-bis(3,5-dihalogeno-4-hydroxyphenyl) propane derivative represented by formula (2)

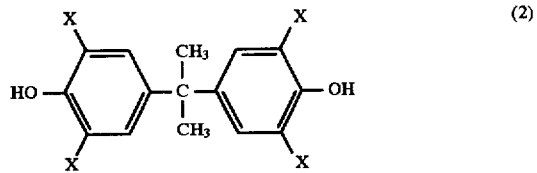 (2)

wherein each X represents a halogen atom, with a metal alkoxide represented by formula (3)

$(R^2O)_nM$ (3)

wherein each $R^2$ represents a lower alkyl group, M represents an alkali metal or an alkaline earth metal, and n represents an integer of 1 or 2.

3. A process for producing 2,2-bis(3,4,5-trihydroxyphenyl)propane, which is characterized by dealkylating a 2,2-bis[3,5-di(lower alkoxy)-4-hydroxyphenyl]propane derivative.

4. A process for producing pyrogallol, which is characterized by decomposing, with an alkali or an acid, a 2,2-bis (3,5-disubstituted-4-hydroxyphenyl)propane derivative represented by formula (1)

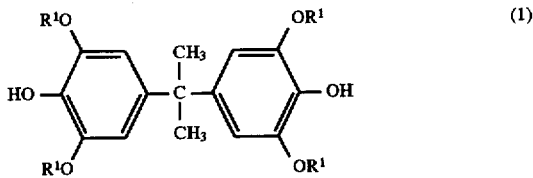 (1)

wherein each $R^1$ represents a hydrogen atom or a lower alkylgroup.

* * * * *

UNITED STATES PATENT AND TRADEMARK OFFICE
CERTIFICATE OF CORRECTION

PATENT NO. : 5,710,346
DATED : JANUARY 20, 1998
INVENTOR(S) : MASAKAZU TAKAHASHI, ET AL.

It is certified that error appears in the above-identified patent and that said Letters Patent is hereby corrected as shown below:

Column 4,    line 2, "hydrogen halides"
    should read --hydrohalic acids--.

Column 4,    line 22, "propane (4) with an"
    should read --propane (I) with an --.

Column 5,    line 41, "2-(3,5"
    should read --2,2-bis(3,5--.

Column 5,    line 65, "hydrogen bromide"
    should read --hydrobromic acid--.

Column 6    line 13, "hydrogen bromide"
    should read --hydrobromic acid--.

Signed and Sealed this

First Day of September, 1998

BRUCE LEHMAN

Attest:

Attesting Officer

Commissioner of Patents and Trademarks